(12) United States Patent
Yahata

(10) Patent No.: US 12,216,083 B2
(45) Date of Patent: Feb. 4, 2025

(54) METHOD FOR DETECTING PRESENCE/ABSENCE OF LIQUID SUCTIONED BY SYRINGE PUMP, AND DEVICE WITH SYRINGE PUMP

(71) Applicant: SHIMADZU CORPORATION, Kyoto (JP)

(72) Inventor: Masahito Yahata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 652 days.

(21) Appl. No.: 17/418,135

(22) PCT Filed: Jun. 17, 2019

(86) PCT No.: PCT/JP2019/023813
§ 371 (c)(1),
(2) Date: Jul. 23, 2021

(87) PCT Pub. No.: WO2020/136944
PCT Pub. Date: Jul. 2, 2020

(65) Prior Publication Data
US 2022/0099626 A1  Mar. 31, 2022

(30) Foreign Application Priority Data
Dec. 27, 2018 (JP) ................. 2018-244142

(51) Int. Cl.
*G01N 27/60* (2006.01)
*G01N 33/18* (2006.01)
*G01N 35/10* (2006.01)

(52) U.S. Cl.
CPC ........... *G01N 27/605* (2013.01); *G01N 33/18* (2013.01); *G01N 35/1016* (2013.01); *G01N 35/1097* (2013.01)

(58) Field of Classification Search
None
See application file for complete search history.

(56) References Cited

U.S. PATENT DOCUMENTS 10,627,384 B1 * 4/2020 Kitada ................. G01N 21/59
2003/0087443 A1   5/2003 Pressman et al.
(Continued)

FOREIGN PATENT DOCUMENTS

CN  1297140 A  5/2001
CN  101308158 A * 11/2008 ......... G01N 35/1009
(Continued)

OTHER PUBLICATIONS

English translation of EP 0694784 A1 (Year: 1996).*
(Continued)

*Primary Examiner* — Jermele M Hollington
(74) *Attorney, Agent, or Firm* — Sughrue Mion, PLLC

(57) ABSTRACT

Provided is method of detecting presence or absence of a liquid suctioned by a syringe pump. The method includes, in a following order: a step of detecting a change in electrostatic capacitance between a pair of electrodes provided to a syringe, having a tubular shape in which a piston is moved in an axial direction of the syringe, of a syringe pump; and a step of detecting that liquid suction has been performed by the syringe pump based on the change in the electrostatic capacitance.

7 Claims, 3 Drawing Sheets

(56) References Cited

U.S. PATENT DOCUMENTS

| | | | |
|---|---|---|---|
| 2010/0199788 A1 | 8/2010 | Ayliffe et al. | |
| 2014/0142537 A1* | 5/2014 | Gibson | A61M 5/14546 604/67 |
| 2015/0268656 A1 | 9/2015 | Bammer et al. | |
| 2018/0361059 A1 | 12/2018 | Gibson et al. | |
| 2022/0299539 A1* | 9/2022 | Horie | G01F 23/263 |

FOREIGN PATENT DOCUMENTS

| | | | | |
|---|---|---|---|---|
| CN | 103813819 A | | 5/2014 | |
| EP | 694784 A1 | * | 1/1996 | ....... G01N 35/00603 |
| JP | 57-153221 A | | 9/1982 | |
| JP | 06-194212 A | | 7/1994 | |
| JP | 2005-506535 A | | 3/2005 | |
| JP | 2007-064759 A | | 3/2007 | |
| JP | 2013-193319 A | | 9/2013 | |
| JP | 2014-525788 A | | 10/2014 | |
| JP | 2015-532136 A | | 11/2015 | |
| JP | 2018-36084 A | | 3/2018 | |
| JP | 2018051064 A | * | 4/2018 | |
| WO | 2006/080761 A1 | | 8/2006 | |

OTHER PUBLICATIONS

English translation of CN 101308158 A (Year: 2008).*
English translation of JP 2018-51064 A (Year: 2018).*
International Search Report for PCT/JP2019/023813 dated Aug. 27, 2019 [PCT/ISA/210].
Written Opinion for PCT/JP2019/023813 dated Aug. 27, 2019 [PCT/ISA/237].
Notice of Reasons for Refusal dated Jan. 18, 2022 from the Japanese Patent Office in JP Application No. 2020-562314.
Communication dated Jun. 21, 2022, issued in Japanese Application No. 2020-562314.
Communication dated May 23, 2022, issued in Chinese Application No. 201980086424.5.
European Office action dated Sep. 4, 2023 in Application No. 19 902 928.1.
Extended European Search Report dated Jul. 29, 2022 from the European Patent Office in EP Application No. 19902928.1.
Communication dated Oct. 16, 2024, issued by the European Patent Office in Application No. 19902928.1.

* cited by examiner

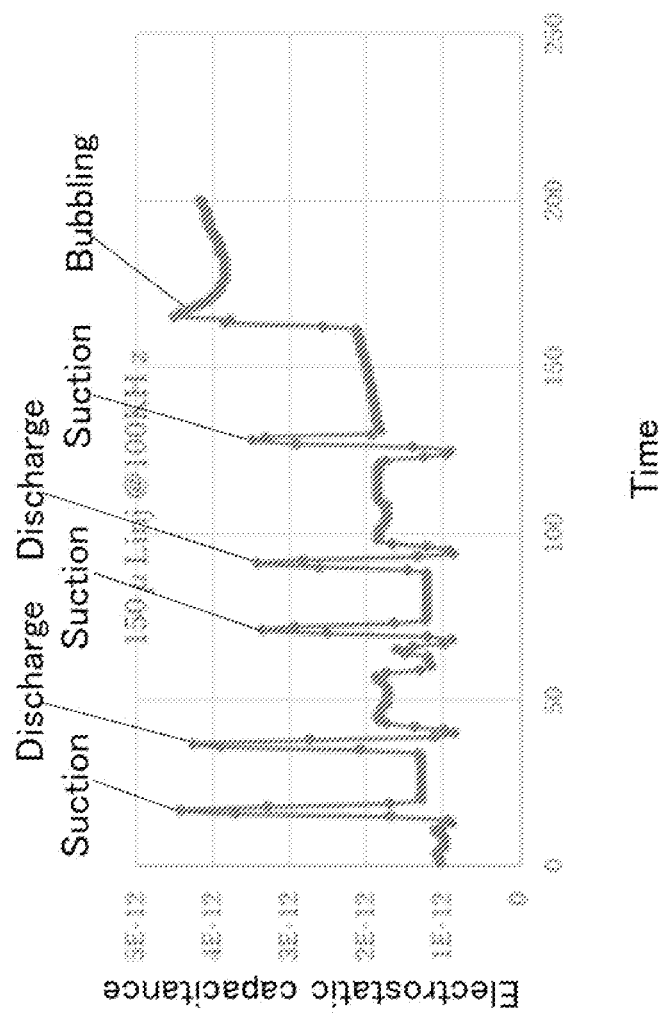

METHOD FOR DETECTING PRESENCE/ABSENCE OF LIQUID SUCTIONED BY SYRINGE PUMP, AND DEVICE WITH SYRINGE PUMP

TECHNICAL FIELD

The present invention relates to a method for detecting the presence/absence of a liquid suctioned by a syringe pump, and a device with a syringe pump.

BACKGROUND ART

In a water quality analyzer such as a total organic carbon measurement device (TOC meter) or a total phosphorus measurement device (TP meter), a syringe pump is used to transfer, besides sample water, a liquid such as a cleaning liquid, an oxidizing agent or a reducing agent (see, for example, Patent Document 1).

PRIOR ART DOCUMENT

Patent Document

Patent Document 1: Japanese Patent Laid-Open No. 2018 059788

SUMMARY OF THE INVENTION

Problems to be Solved by the Invention

In the water quality analyzer as described above, measurement cannot be normally performed unless suction and discharge of a liquid by the syringe pump are normally performed. When sampling of the sample water is not normally performed, a measured value obtained after such sampling exhibits an abnormal value. In this case, however, it is not easy to identify that such an abnormal measured value is exhibited due to a failure in sampling water by the syringe pump.

As a cause of the failure in water sampling by the syringe pump, in addition to a case where the syringe pump is not normally operated, a case is considered where, although the syringe pump is normally operated, a liquid is not normally suctioned into the syringe pump. Whether or not the syringe pump is operated normally can be detected by monitoring driving of a motor that operates the syringe pump. On the other hand, since it is difficult to insert a liquid level sensor into a syringe of the syringe pump, it is impossible to detect by the liquid level sensor whether or not the syringe pump has actually suctioned a liquid normally.

In view of such circumstances, it is an object of the present invention to provide a technique by which the presence or absence of a liquid suctioned by a syringe pump can be automatically detected.

Solutions to the Problems

A method according to the present invention includes, in a following order: a step of detecting a change in electrostatic capacitance between a pair of electrodes provided to a syringe, having a tubular shape in which a piston is moved in an axial direction of the syringe, of a syringe pump; and a step of detecting that liquid suction has been performed by the syringe pump based on the change in the electrostatic capacitance.

A liquid and air differ from each other in dielectric constant (a dielectric constant of air being about 1/80 of a dielectric constant of water). Accordingly, an amount of electrostatic capacitance in a space in the syringe largely differs between a case where a liquid phase exists in the space and a case where an air phase exists in the space. Therefore, it can be detected that liquid suction has been performed by the syringe pump by detecting a change in electrostatic capacitance in the space in the syringe.

In the first configuration of the method according to the present invention, in the step of detecting the liquid suction, it is detected that the liquid suction has been performed by the syringe pump when a value of the electrostatic capacitance exceeds a preset threshold, or when a value that changes in conjunction with the change in the electrostatic capacitance exceeds a preset threshold. With such a configuration, it can be easily detected that liquid suction has been performed by the syringe pump.

In the second configuration of the method according to the present invention, the pair of electrodes is attached on an outer peripheral surface of the syringe in a spaced-apart manner from each other in the axial direction of the syringe. With such a configuration, it is possible to realize the detection of the suction of the liquid by the syringe pump with a simple and inexpensive configuration.

The first configuration and the second configuration can be combined with each other.

A device according to the present invention includes a syringe pump, a pair of electrodes, a detector, and a liquid suction detector. In the syringe pump, a piston is moved in a tubular syringe in an axial direction of the syringe. The pair of electrodes is provided to the syringe so that electrostatic capacitance between the pair of electrodes changes between when the liquid suction into the syringe is performed and when the liquid suction into the syringe is not performed. The detector detects a value of electrostatic capacitance between the pair of electrodes or a value that changes in conjunction with a change in the electrostatic capacitance. The liquid suction detector detects that the liquid suction has been performed by the syringe pump based on the change in electrostatic capacitance between the pair of electrodes detected by the detector or the change in the value that changes in conjunction with the change in the electrostatic capacitance.

That is, the device according to the present invention has a function of automatically detecting the presence or absence of liquid suction by the syringe pump based on a change in electrostatic capacitance between the pair of electrodes provided to the syringe of the syringe pump.

In the first configuration of the device according to the present invention, the pair of electrodes is attached on an outer peripheral surface of the syringe in a spaced-apart manner from each other in an axial direction of the syringe.

In the second configuration of the device according to the present invention, the liquid suction detector detects that the liquid has been suctioned by the syringe pump when the value of electrostatic capacitance between the pair of electrodes exceeds a preset threshold, or when the value that changes in conjunction with the change in the electrostatic capacitance exceeds a preset threshold. With such a configuration, it can be easily detected that liquid suction has been performed by the syringe pump.

In the third configuration of the device according to the present invention, the pair of electrodes includes aluminum thin films wrapped around an outer peripheral surface of the syringe at two positions. With such a configuration, it is possible to realize a function of detecting the suction of the liquid by the syringe pump with a simple and inexpensive configuration.

The above first to third configurations of the device according to the present invention can be combined with each other.

Effects of the Invention

According to the method and the device of the present invention, it is possible to automatically detect the presence or absence of a liquid suctioned by the syringe pump.

BRIEF DESCRIPTION OF THE DRAWINGS

FIG. 3 is a graph illustrating a relationship between an operation of a syringe pump and a detection signal (electrostatic capacitance) of a detector.

EMBODIMENT OF THE INVENTION

Hereinafter, an embodiment of a method of detecting the presence or absence of a liquid suctioned by a syringe pump and a device having a function of detecting the presence or absence of a liquid suctioned by the syringe pump will be described with reference to the drawings.

Figure 1:
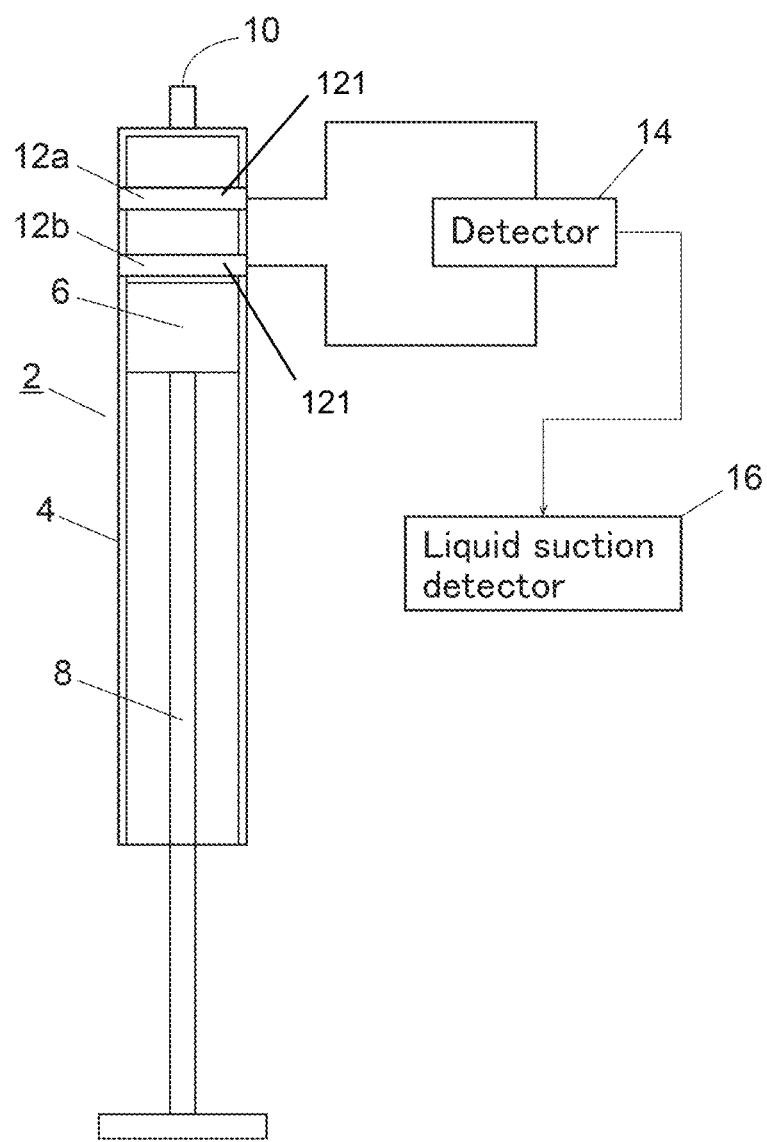
FIG. 1 is a schematic configurational view illustrating an embodiment of a water quality analyzer.

FIG. 1 shows a schematic configuration of a device having a function of detecting the presence or absence of a liquid suctioned by a syringe pump.

A syringe pump 2 includes: a tubular syringe 4 having a suction/discharge port 10 at a distal end of the syringe 4 for sucking and discharging a liquid; a piston 6 being operable in the syringe 4 in an axial direction (a vertical direction in the drawing) of the syringe 4; and a piston rod 8 for holding the piston 6 at a distal end of the piston rod 8 and for driving the piston 6.

A pair of electrodes 12a, 12b is provided to the syringe 4 of the syringe pump 2. The pair of electrodes 12a, 12b are provided to an outer peripheral surface of the syringe 4 of the syringe pump 2 on a distal end side of the syringe 4 in a spaced-apart manner from each other in an axial direction of the syringe 4. The pair of electrodes 12a, 12b is each formed of, for example, an aluminum thin film 121 wound around the outer peripheral surface of the syringe pump 2. A detector 14 is electrically connected to the pair of electrodes 12a, 12b. The detector 14 detects a value of electrostatic capacitance between the pair of electrodes 12a, 12b or a value (for example, reactance or impedance) that changes corresponding to a change in electrostatic capacitance. As the detector 14, an LCR meter can be used. The pair of electrodes 12a, 12b may be configured such that electrostatic capacitance between the electrodes 12a, 12b changes between when the suction of a liquid into the syringe 4 is performed and when the suction of the liquid into the syringe 4 is not performed, that is, between when a liquid phase exists between the electrodes 12a, 12b and when the liquid phase does not exist between the electrodes 12a, 12b.

The water quality analyzer further includes a liquid suction detector 16. The liquid suction detector 16 is configured to detect that a liquid has been suctioned by the syringe pump 2 based on a change in a detection signal transmitted from the detector 14. The liquid suction detector 16 is a function realized by an arithmetic element such as a central processing unit (CPU) and a predetermined program executed by the arithmetic element.

In a state where no liquid is suctioned into the syringe 4, an air layer exists in a space in the syringe 4 formed between the pair of electrodes 12a, 12b. When the liquid is suctioned into the syringe 4 so that the space in the syringe 4 between the pair of electrodes 12a, 12b becomes a liquid layer, the electrostatic capacitance between the pair of electrodes 12a, 12b increases due to the difference in dielectric constant between water and air. The liquid suction detector 16 is configured to detect a change in electrostatic capacitance between the pair of electrodes 12a, 12b based on a change in a detection signal value of the detector 14, and is configured to detect that the liquid has been suctioned by the syringe pump 2 based on the change in electrostatic capacitance between the pair of electrodes 12a, 12b.

As the method of detecting that a liquid has been suctioned by the syringe pump 2 based on a change in a detection signal value of the detector 14, a method is considered where a detection signal value of the detector 14 is compared with a preset threshold, and it is detected that the liquid is suctioned into the syringe 4 of the syringe pump 2 when the detection signal value exceeds the threshold.

Figure 2:
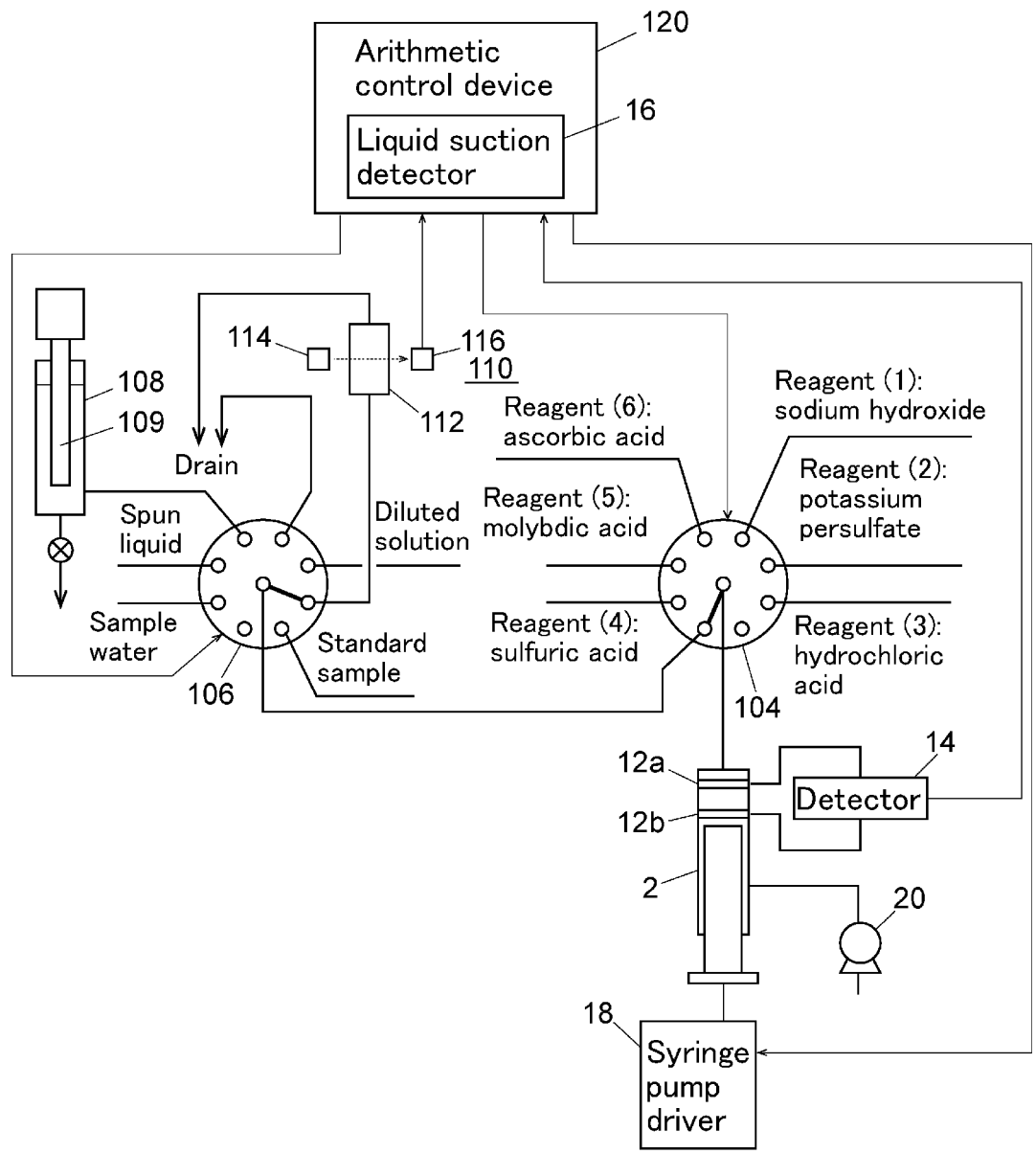
FIG. 2 is a flowchart illustrating an example of a reagent determination operation of the embodiment.

Next, the water quality analyzer which is an embodiment of a device having a function of detecting a liquid suctioned by the syringe pump 2 will be described with reference to FIG. 2.

The water quality analyzer of this embodiment mainly includes the syringe pump 2, two multi-port valves 104, 106, a reactor 108, a measurement unit 110, and an arithmetic control device 120.

A suction/discharge port of the syringe pump 2 is connected to a center port of the multi-port valve 104 described later. A pump 20 for stirring is connected to the cylinder of the syringe pump 2 through a flow path, and liquid can be stirred in the syringe pump 2 by air supplied by the pump 20. The syringe pump 2 is driven by a syringe pump driver 18 which includes a stepping motor and the like.

The multi-port valve 104 has one center port and a plurality of select ports, and the center port can be selectively connected to any one of the select ports. One select port of the multi-port valve 104 is connected to a center port of the multi-port valve 106 through a flow path. The other select ports of the multi-port valve 104 are ports to which containers that store reagents (1) to (6) are connected respectively.

In this example, a sodium hydroxide solution is provided as the reagent (1), a potassium persulfate solution is provided as the reagent (2), a hydrochloric acid solution is provided as the reagent (3), a sulfuric acid solution is provided as the reagent (4), a molybdic acid solution is provided as the reagent (5), and an ascorbic acid solution is provided as the reagent (6). The arithmetic control device 120 that controls the operation of the water quality analyzer stores the select ports of the multi-port valve 4 and the reagents (1) to (6) to be connected to the select ports in a state where the select ports and the reagents (1) to (6) correspond to each other.

The multi-port valve 106 also has one center port and a plurality of select ports, and the center port is selectively connected to any one of the select ports. One select port of the multi-port valve 106 is connected to the reactor 108 through a flow path, and another select port of the multi-port valve 106 is connected to an inlet of a measurement cell 112 of the measurement unit 110 through a flow path. To other select ports of the multi-port valve 106, a water sampling tube for sampling sample water, and flow paths communicating with containers which respectively store a spun liquid, a diluted liquid, and a standard liquid are connected.

The reactor 108 is provided for applying an oxidation treatment to a sample. The reactor 108 has an inner space for storing liquid, and a lighting portion of an ultraviolet ray lamp 109 is inserted into the inner space. The oxidation treatment of a sample is a treatment where a compound to be measured in the sample is oxidatively decomposed by irradiating ultraviolet rays to the sample to which an oxidizing agent (for example, a potassium persulfate solution) is added while supplying oxygen gas or air into the inner space of the reactor 108 under a predetermined temperature condition (for example, 95° C.)

The measurement unit 110 includes the measurement cell 112, a light source 114, and a light detection element 116. An outlet of the measurement cell 112 communicates with a drain. The light source 114 generates light having a measurement wavelength (for example, 220 nm) and irradiates the light toward the measurement cell 112. As the light source 114, for example, a laser element can be used. The light detection element 116 is provided for detecting the intensity of light from the light source 114 that has passed through the measurement cell 112. As the light detection element 116, for example, a photodiode can be used.

Sample water to which oxidizing treatment is already applied or any one of the reagents (1) to (6) is selectively transferred to the measurement cell 112 of the measurement unit 110 by the syringe pump 2.

The arithmetic control device 120 is provided for performing an operation control and arithmetic processing of the water quality analyzer. As the arithmetic control device 120, a dedicated computer or a general-purpose personal computer can be used. A detection signal from the detector 14 that detects a value of electrostatic capacitance between the pair of electrodes 12a, 12b provided to the syringe 4 of the syringe pump 2 or a value that changes corresponding to a change in electrostatic capacitance is taken into the arithmetic control device 120. The arithmetic control device 120 includes the liquid suction detector 16 that is configured to detect the suction of a liquid by the syringe pump 2 based on a change in a detection signal of the detector 14. The liquid suction detector 16 is realized when a CPU that is incorporated in the arithmetic control device 120 executes a predetermined program.

The arithmetic control device 120 controls an operation of the syringe pump driver 18. The arithmetic control device 120 can check whether or not a liquid suctioned by the syringe pump 2 is actually performed by taking in a detection signal from the detector 14 at a timing that the syringe pump 2 is operated so as to perform a suction operation of the liquid. That is, when the liquid suction detector 16 does not detect the suction of a liquid by the syringe pump 2 even though a signal to request the syringe pump 2 to execute the suction of the liquid is transmitted to the syringe pump driver 18, the arithmetic control device 120 can detect that an error has occurred in the suction of the liquid by the syringe pump 2.

FIG. 3 is a graph illustrating an example of a relationship between an operation of the syringe pump 2 and a detection signal value (electrostatic capacitance) of the detector 14. As can be understood from FIG. 3, peaks appear in the detection signal of the detector 14 at timings when the syringe pump 2 suctions and discharges the liquid. The detection signal has a peak shape because the syringe pump 2 is operated such that air is suctioned after a predetermined amount of liquid is suctioned into the syringe of the syringe pump 2 so that a liquid phase temporarily passes through the space between the pair of electrodes 12a, 12b. Further, the detection signal of the detector 14 is in an elevated state also during a period where bubbling is performed by feeding air into the syringe pump 2 by the pump 20 after the liquid is suctioned into the syringe pump 2. This is because a splash of liquid reaches a space between the pair of electrodes 12a, 12b during bubbling and hence, electrostatic capacitance between the pair of electrodes 12a, 12b increases.

In this manner, by providing the liquid suction detector 16 to a device such as the water quality analyzer that uses the syringe pump 2, it is possible to monitor whether or not an operation such as a suction operation or a discharge operation of liquid by the syringe pump 2 is normally performed.

DESCRIPTION OF REFERENCE SIGNS

2: Syringe pump
4: Cylinder
6: Piston
8: Piston rod
10: Suction/discharge port
12a, 12b: Electrode
14: Detector
16: Liquid suction detector

The invention claimed is:

1. A method comprising, in a following order:
a step of detecting an electrostatic capacitance within a syringe, the electrostatic capacitance being detected between a pair of electrodes provided to the syringe, the syringe having a tubular shape in which a piston is moved in an axial direction of the syringe, of a syringe pump;
a step of detecting a change in the electrostatic capacitance between the pair of electrodes provided to the syringe; and
a step of detecting that liquid suction has been performed by the syringe pump based on the change in the electrostatic capacitance.

2. The method according to claim 1, wherein the step of detecting the liquid suction includes determining that the liquid suction has been performed by the syringe pump when a value of the electrostatic capacitance exceeds a preset threshold, or when a value that changes in conjunction with the change in the electrostatic capacitance exceeds a preset threshold.

3. The method according to claim 1, wherein the pair of electrodes is attached on an outer peripheral surface of the syringe in a spaced-apart manner from each other in the axial direction of the syringe.

4. A device comprising:
a syringe pump comprising:
a syringe having a tubular shape, and
a piston operated in the syringe in an axial direction of the syringe;
a pair of electrodes provided to the syringe and configured to measure an electrostatic capacitance within the syringe between the pair of electrodes such as to determine when a liquid suction into the syringe has been performed and when the liquid suction into the syringe has not been performed;
a detector configured to detect a value of electrostatic capacitance between the pair of electrodes or a value that changes in conjunction with a change in the electrostatic capacitance; and
a liquid suction detector configured to detect that the liquid suction by the syringe pump has been performed based on the change in electrostatic capacitance between the pair of electrodes or the change in the value that changes in conjunction with the change in the electrostatic capacitance detected by the detector.

5. The device according to claim 4, wherein the pair of electrodes is attached on an outer peripheral surface of the syringe in a spaced-apart manner from each other in an axial direction of the syringe.

6. The device according to claim 4, wherein the liquid suction detector is configured to detect that the liquid has been suctioned by the syringe pump when the value of electrostatic capacitance between the pair of electrodes exceeds a preset threshold, or when the value that changes in conjunction with the change in the electrostatic capacitance exceeds a preset threshold.

7. The device according to claim 4, wherein the pair of electrodes comprises aluminum thin films wrapped around an outer peripheral surface of the syringe at two positions.

* * * * *